US006429320B1

United States Patent
McCurry, Jr. et al.

(10) Patent No.: US 6,429,320 B1
(45) Date of Patent: Aug. 6, 2002

(54) PROCESSES FOR THE PURIFICATION OF TOCOPHEROL AND/OR STEROL COMPOUNDS AND COMPOSITIONS CONTAINING ORTHOBORATE ESTER MIXTURES

(75) Inventors: Patrick M. McCurry, Jr., West Chester; Stephen W. Turner, Hamilton; Carl Pickens, deceased, late of West Chester, all of OH (US), by Jan R. Varvil, Administratrix

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/922,208

(22) Filed: Aug. 3, 2001

Related U.S. Application Data

(60) Provisional application No. 60/223,217, filed on Aug. 4, 2000.

(51) Int. Cl.$^7$ ............................................. C07D 311/76
(52) U.S. Cl. ........................ 549/413; 549/407; 549/408; 552/547
(58) Field of Search ................................. 549/407, 408, 549/413; 552/547

(56) References Cited

U.S. PATENT DOCUMENTS

| | | | |
|---|---|---|---|
| 4,550,183 A | 10/1985 | Willging | 549/413 |
| 4,617,406 A | 10/1986 | Willging | 549/413 |
| 5,487,817 A | 1/1996 | Fizet | 203/38 |
| 5,892,058 A | 4/1999 | Brüggemann et al. | 549/412 |

FOREIGN PATENT DOCUMENTS

WO  WO 01/60409 A1  8/2001

*Primary Examiner*—Amelia Owens
(74) *Attorney, Agent, or Firm*—John E. Drach; Aaron R. Ettelman

(57) ABSTRACT

Processes for purifying compounds are disclosed which include reacting (i) a mixture of at least one tocopherol compound or sterol compound, and an alcohol having from about 10 to 30 carbons with (i) one or more boron-containing compounds to form a second mixture of orthoborate esters, wherein the mole ratio of tocopherol, sterol and alcohol to boron is at least about 2.5:1; heating the second mixture to form a residue containing the orthoborate esters; contacting the residue with a compound capable of solvolyzing the orthoborate esters to form a third mixture including the boron-containing compound(s), the alcohol and the tocopherol and/or sterol compound(s); and recovering the tocopherol and/or sterol compound(s). Another process for purifying such compounds includes an activated carbon treatment, which may alternatively follow the other process steps; formation of borate esters; heating to remove low boiling point components; formation of a residue comprising the borate esters; contacting the residue with a compound capable of solvolyzing the borate esters; and separation of the remaining components. Compositions including mixtures of alkyl/tocopherol/sterol orthoborate esters are also disclosed.

52 Claims, No Drawings

PROCESSES FOR THE PURIFICATION OF TOCOPHEROL AND/OR STEROL COMPOUNDS AND COMPOSITIONS CONTAINING ORTHOBORATE ESTER MIXTURES

CROSS-REFERENCE TO RELATED APPLICATIONS

This application claims priority, under 35 U.S.C. §119(e), of provisional U.S. patent application Ser. No. 60/223,217, which was filed on Aug. 4, 2000, the entire contents of which are incorporated herein by reference.

BACKGROUND OF THE INVENTION

As concerns over maintaining proper health continue to grow, vitamin and antioxidant use and intake also continue to rise. As more evidence of the potential benefits associated with the use and intake of vitamins and antioxidants continues to be generated, demand for such substances increases, as does the demand for purer forms thereof. Many antioxidants and vitamins can be found in, and extracted from, natural sources. However, these natural sources, e.g., plants and vegetables, contain many undesirable components and impurities which are extracted along with the antioxidants.

For example, tocopherol compounds are components of vegetable oils which exhibit vitamin E activity. Tocopherol compounds are found widely distributed in many organic substances, including grain oils and vegetable oils. However, the amount of tocopherol present in the natural oils may be small, and therefore, the oils are distilled to concentrate the tocopherol content. Unfortunately, the content of other undesirable co-boilers, as well as pesticides, fertilizers, etc. may also be concentrated.

As such, there have been many attempts to recover and purify antioxidants, such as tocopherols, from natural sources. For example, a method which involves mixing a tocopherol-containing material with a polar organic solvent and contacting this mixture with a strongly basic anionic exchange resin, whereby the tocopherols are absorbed onto the resin, and subsequently eluted with an acidic solution, has been described. However, such methods can result in resin fouling, and potential oxidation of the resins may result in a persistent amine odor. Moreover, resins are short-lived, expensive and provide relatively low capacity.

Other processes for the isolation of tocopherols involve treating deodorizer distillates, which comprise the "sludge" or distillate obtained in connection with the production of edible oils and fats subsequent to the deodorization step, with a lower aliphatic alcohol in the presence of an acid catalyst, often with prior saponification of the sludge, for the purposes of esterifying the free fatty acids present in the sludge. Other processes have been disclosed wherein the tocopherols and/or sterols are esterified with the free fatty acids contained in the distillates. However, these processes are often complicated, time-consuming and expensive. Moreover, most prior art processes for the purification or isolation of tocopherols and/or sterols which involve the esterification of the tocopherols and/or sterols with free fatty acids present in the feed are incapable of adequately removing impurities and other components which co-distill with tocopherols and/or sterols, at sufficient yields.

Another process for the separation of tocopherols has been described wherein borate esters are formed, the mixture is distilled and the esters are subsequently hydrolyzed, with subsequent separation of the borate source from the tocopherol. While such a process generally removes a large portion of the impurities that co-distill with the tocopherol, significant amounts of the tocopherol in the original feed material can be lost during the purification, foaming during the esterification process is a significant problem, and undesirable borate solids can form requiring additional separation steps.

Thus, there is a need in the art for a process by which tocopherol and/or sterol compounds can be purified in high yield from natural sources with suitably high degrees of purity.

BRIEF SUMMARY OF THE INVENTION

The present invention relates to processes for the purification of compounds, such as tocopherol and/or sterol compounds, from natural sources, wherein a high yield is obtained, in addition to a high degree of purity. The processes according to the present invention provide purified tocopherols and sterols from natural sources at unexpectedly high and significantly improved yields and further remove many of the unwanted components which co-distill with tocopherols and/or sterols, as well as impurities and other undesirable components to negligible amounts and even undetectable levels.

The present invention includes a process for purifying compounds, wherein the process comprises: (a) providing a first mixture comprising at least one compound selected from the group consisting of tocopherol compounds and sterol compounds, and an alcohol having from about 10 to about 30 carbon atoms; (b) reacting the first mixture with one or more boron-containing compounds selected from the group consisting of boric acid, alkoxy borates, alkoxy boroxines, phenoxy borates and phenoxy boroxines to form a second mixture comprising one or more orthoborate esters, wherein the mole ratio of combined tocopherol, sterol and alcohol to boron is at least about 2.5:1; (c) heating the second mixture to remove low boiling point components to form a residue comprising the one or more orthoborate esters; (d) contacting the residue with one or more compounds capable of solvolyzing the one or more orthoborate esters to form a third mixture comprising one or more resulting boron-containing compounds, the alcohol and the at least one compound selected from the group consisting of tocopherol compounds and sterol compounds; and (e) recovering the at least one compound selected from the group consisting of tocopherol compounds and sterol compounds.

In accordance with preferred embodiments of the present invention, the alcohol comprises oleyl alcohol or dodecyl alcohol, the boron-containing compound comprises boric acid, the mole ratio of combined tocopherol, sterol and alcohol to boron is at least about 3:1; and step (c) is carried out at a temperature which is about 60° C. greater than the boiling point of the at least one compound selected from the group consisting of tocopherol compounds and sterol compounds, under reduced pressure.

The present invention also includes a process for purifying compounds, said process comprising: (a) subjecting a composition comprising at least one compound selected from the group consisting of tocopherol compounds and sterol compounds to an activated carbon pretreatment; (b) combining the pretreated composition with one or more boron-containing compounds selected from the group consisting of boric acid, alkoxy borates, alkoxy boroxines, phenoxy borates and phenoxy boroxines to form a mixture comprising one or more borate esters; (c) heating the mixture to remove low boiling point components to form a residue comprising the one or more borate esters; (d) contacting the residue with one or more compounds capable of solvolyzing the one or more borate esters to form a second mixture comprising one or more resulting boron-containing compounds and the at least one compound selected from the group consisting of tocopherol compounds and sterol compounds; and (e) separating the one or more resulting boron-containing compounds and the at least one compound selected from the group consisting of tocopherol compounds and sterol compounds.

Furthermore, the present invention includes a composition comprising a mixture of trialkyl orthoborate esters, dialkyl-monotocopherol orthoborate esters, and monoalkyl-ditocopherol orthoborate esters. A composition in accordance with the present invention may further comprise dialkyl-monosterol orthoborate esters, monoalkyl-disterol orthoborate esters and monoalkyl-monotocopherol-monosterol orthoborate esters. Additionally, the present invention includes a composition prepared by a process comprising: (a) combining a composition comprising at least one compound selected from the group consisting of tocopherol compounds and sterol compounds with an alcohol having from about 10 to about 30 carbon atoms to form a first mixture; (b) reacting the first mixture with one or more boron-containing compounds selected from the group consisting of boric acid, alkoxy borates, alkoxy boroxines, phenoxy borates and phenoxy boroxines to form a second mixture comprising one or more orthoborate esters, wherein the mole ratio of combined tocopherol, sterol and alcohol to boron is at least about 2.5:1; and (c) heating the second mixture to remove low boiling point components to form a mixture comprising the one or more orthoborate esters.

DETAILED DESCRIPTION OF THE INVENTION

The present invention is directed to processes for the purification of compounds such as, for example, tocopherol compounds and sterol compounds. As used herein, the term "tocopherol compounds" refers to the broad class of compounds which can be characterized as derivatives of 6-chromanol having an isoprenoid side chain, of which many are known to exhibit vitamin E activity. These compounds include, for example, the alpha (α:-), beta (β-), gamma (γ-) and delta (δ-) homologues of tocopherol, as well as unsaturated derivatives, such as, tocomonoenols, tocodienols and tocotrienols. As used herein, the term "sterol compounds" refers to the broad class of compounds also known as steroid alcohols, which possess a steroid nucleus of four fused carbon rings with a hydroxyl group present in addition to any other side chains, for example, an 8 to 10 carbon side chain. As used herein, "sterol compounds" refer to both plant- and animal-derived steroidal alcohols, including, for example, cholesterol and phytosterols including, but not limited to, sitosterol and campesterol, as well as the hydrogenated versions thereof known as stanols.

Compositions which contain at least one tocopherol compound or sterol compound (hereinafter also referred to as "starting compositions") which may be subjected to the purification process in accordance with the present invention include, for example, natural organic sources such as grain oils, vegetable oils and plant sources. Examples of suitable grain and vegetable oils include wheatgerm, corn, barley, rye, safflower, soybean, peanut, cottonseed, linseed, sunflower, rapeseed and palm oils. Examples of suitable plant sources from which the starting composition may be derived include palm leaves, lettuce, alfalfa, rubber latex and a variety of other plant materials. The natural sources for use in the present invention are available commercially and can also be extracted via known techniques.

The amount of tocopherol compound or sterol compound present in such compositions for use in the present invention may vary widely, and may be as low as about 1% prior to purification by the process of the present invention, or as high as at least about 95%. Often, vegetable oils are distilled to produce a concentrate that is up to about 60% mixed tocopherols. Such vegetable oil concentrates can also be used as compositions containing tocopherol and/or sterol compounds to be purified in accordance with the present invention.

A first mixture in accordance with the present invention will contain an alcohol which may be added to a starting composition, or a starting composition which already contains a suitable alcohol may be used. For example, many vegetable oil distillates may contain various fatty alcohols in varying amounts. In some instances, a starting composition may contain some alcohol, and further alcohol may be added to provide a first mixture.

Suitable alcohols, which may be present in a first mixture in accordance with the present invention, either naturally to some degree or by combination with a tocopherol compound and/or a sterol compound, include primary or secondary alcohols, which may be saturated or unsaturated, branched or linear and cyclic or acyclic having from about 10 to about 30 carbon atoms, or phenols. Alcohols used in accordance with the present invention will preferably have from about 12 to about 26 carbon atoms, and more preferably from about 12 to about 20 carbon atoms. Alcohols with less than 12 carbons, such as n-decanol, may be used in accordance with the present invention, however the volatility of the tridecylborate formed during reaction of the alcohol and the boron-containing compound(s) is high enough that large portions of the alcohol are lost along with the co-boiling fraction of the initial starting material during the heating step, leading to lower recovery of tocopherols and/or sterols. Thus, alcohols with 12 or more carbon atoms are preferred. Moreover, alcohols with more than 26 carbon atoms may be used in accordance with the present invention, however separation of the alcohol from the recovered tocopherol and/or sterol becomes more difficult, leading to lower purity. Thus, alcohols with 26 or less carbon atoms are preferred.

The most preferred alcohols for use in accordance with the present invention will have from about 12 to about 18 carbon atoms. Examples of alcohols which may be used in accordance with preferred embodiments of the present invention include, but are not limited to, dodecanol, tetradecanol, hexadecanol, octadecanol, oleyl alcohol, isostearyl alcohol, Guerbet alcohols, particularly $C_{16}$ Guerbet alcohol (i.e., 2-hexyldecanol), and mixtures thereof Stearyl alcohol, or octadecanol, is an alcohol found in most vegetable oil distillates, and is further preferred since lower amounts will need to be added to a first mixture in accordance with the present invention. Alcohols which can be used in accordance with the present invention are common and well known and can be obtained commercially or prepared via known methods.

In accordance with one embodiment of the present invention, wherein a composition containing a tocopherol compound and/or a sterol compound is combined with one or more alcohols, as described above, to form a first mixture, the composition and the alcohol component may be combined in any manner sufficient to allow mixing of the components. The method of combination and container are not critical, and can include, for example, introducing the components, simultaneously or in any order, into a container with stirring by mechanical agitation. Preferably, the components will be combined in a container which is capable of withstanding the heat applied subsequently in the process according to the present invention, or in a container adapted for facilitated transfer of the materials to a heating apparatus.

In other preferred embodiments of the present invention, a carbon treatment can be used to enhance the overall purification. Carbon treatments in accordance with the present invention can be employed as a pre-treatment, or as a post-treatment. For example, in certain preferred embodiments of the present invention, a starting composition is subjected to an activated carbon pretreatment either prior to combining the starting composition with an alcohol or before reacting the first mixture with the one or more boron-containing compounds. Alternatively, a tocopherol or sterol compound purified in accordance with the present invention can be subjected to an activated carbon post-treatment. An activated carbon treatment in accordance with such preferred embodiments generally includes contacting either the starting composition, the first mixture, or the purified final compounds with an activated carbon powder for at least 1 minute at a temperature of at least about 50° C., preferably with stirring. It is preferable that the activated carbon powder be present in an amount of at least about 0.25 weight percent based on the total weight of the compound(s) selected from tocopherol compounds and sterol compounds. Selection between pre- and post-treatment is generally a matter of process convenience, although stirring and carbon contact may be easier with the purified compounds as opposed to the starting compounds or first mixtures.

The first mixture, which includes: (1) the composition containing the tocopherol compound(s) and/or the sterol compound(s) in addition to any impurities present in the composition such as, for example, low boiling point components and co-distilling impurities; and (2) the alcohol component, is reacted with one or more boron-containing compounds.

Boron-containing compounds which may be used in accordance with the present invention include, but are not limited to, boric acid, alkoxy borates, alkoxy boroxines, phenoxy borates and phenoxy boroxines. Preferably, the boron-containing compound used in accordance with the present invention will be boric acid, though other boron-containing compounds such as boroxines, also known as metaborates, may be used so long as the overall ratio of hydroxyl-containing species to boron is maintained at a level in accordance with the present invention. Alkoxy and/or phenoxy borates or boroxines used in accordance with the present invention will preferably have up to 30 carbon atoms, more preferably from about 12 to about 26 carbon atoms, and most preferably from about 12 to about 20 carbon atoms.

Boric acid and alkoxy and/or phenoxy borates or boroxines used in accordance with the present invention can be obtained commercially or synthesized by known methods.

The amount of boron-containing compound reacted with the first mixture is an amount which is sufficient to form essentially orthoborate esters. Thus, in accordance with the present invention, the mole ratio of the tocopherol compound(s), sterol compound(s) and alcohol(s), combined, to boron in the boron-containing compound is at least about 2.5:1. Preferably, the mole ratio is at least about 2.75:1, and most preferably the mole ratio is at least about 3:1. The tocopherol compound(s), sterol compound(s) and alcohol(s) can be used in greater excess, however, the maximum preferred mole ratio of these components, for economical reasons, is about 3.5:1. A more preferred maximum mole ratio is about 3.2:1. At mole ratios greater than about 3.5:1, the capacity of a reactor will be reduced. However, larger ratios could be used.

It is essential, in accordance with the process of the present invention, that the mole ratio of the tocopherol compound(s), sterol compound(s) and alcohol(s), combined, to boron in the one or more boron-containing compounds be at least about 2.5:1, in order to form essentially only orthoborate esters of the general formula (I):

(I)

wherein each —OX independently represents a tocopherol, sterol or alcohol residue, bound to the boron atom at its hydroxyl oxygen position, as opposed to metaborate esters or polyborate esters, wherein multiple boron-containing compounds condense to form a heterocyclic boron ester of the general formula (II):

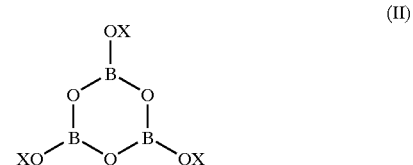

(II)

wherein each —OX is as described above. During the formation of orthoborate esters in accordance with the present invention, competitive reactions may occur if the mole ratio is not kept at or above the levels recited above. For example, competitive dimerization and/or trimerization may occur at lower mole ratios. Thus, for example, where the mole ratio of components is about 2:1, competitive dimerization may occur resulting in polyborate esters of the general formula (III):

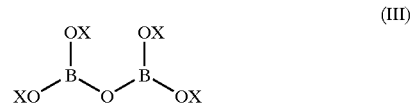

(III)

Polyborate esters of the general formula (m) may fuirther break down into esters of the general formulae (I) and (II), along with other monotocopherol/monosterol orthoborate ester species.

Orthoborate esters of the general formula (I), which may be formed during the reaction in accordance with the present invention include monoalkyl-ditocopherol orthoborate esters, dialkyl-monotocopherol orthoborate esters, monoalkyl-disterol orthoborate esters, dialkyl-monosterol orthoborate esters, and trialkyl borate esters, wherein the alkyl moieties correspond to the alcohol in the first mixture. Other orthoborates which may form during the reaction, though to a lesser degree include mixed alkyiltocopherol/sterol orthoborate esters, tritocopherol orthoborate esters and tristerol orthoborate esters.

The second mixture thus formed includes the one or more orthoborate esters, any unreacted alcohol(s), tocopherol compound(s), sterol compound(s), and/or boron-containing compound(s) which may remain, and the remainder of the original composition containing the tocopherol and/or sterol compound(s), namely impurities such as pesticides, fertilizers, co-boiling hydrocarbons, etc. It is preferable to allow the reaction in which the orthoborate esters are formed to proceed as close to completion as possible, and thus maximize the formation of tocopherol and/or sterol orthoborate esters. While the borate esterification process is reversible and will attain one of several equilibria states if allowed, the reaction can be conducted to shift the reaction so as to maximize ester production, as discussed in more detail below, and thus increase the amount of tocopherol and/or sterol ultimately recovered. The borate esterification process will proceed at room temperature. However, the reaction may be carried out more rapidly at an increased temperature. Thus, in accordance with preferred embodiments of the present invention, the esterification reaction may be carried out at temperatures of from about 40° C. to about 305° C. for a sufficient length of time, and at varying pressures as discussed below. A more preferred temperature is from about 100° C. to about 225° C., and an even more preferred temperature range is from about 160° C. to about 200° C. At temperatures in excess of 100° C., the condensation water produced during the esterification reaction can be substantially eliminated.

Temperatures during the esterification process should also be maintained below the boiling points of the tocopherol and/or sterol compound(s) in order to minimize the loss of the compounds due to their distillation prior to the formation of the one or more orthoborate esters. Materials less volatile than the tocopherol and/or sterol compound(s) and any co-boiling impurities may preferably be removed during esterification by using the preferred higher temperatures previously set forth.

If desired, in order to aid in the removal of the water and other volatiles during the esterification reaction, the pressure during esterification may be lowered. Thus, in accordance with preferred embodiments of the present invention, the esterification reaction may be carried out at pressures of from about atmospheric pressure to as low as 1 mm Hg, or even lower, for example, 0.1 mm Hg, so long as the temperature is maintained low enough to prevent the distillation of the tocopherol and/or sterol compound(s). Thus, when the pressure during esterification is below 1 mm Hg, the temperature should be maintained at or below about 250° C. to ensure that a minimum amount of the tocopherol and/or sterol compound(s) distill. In one preferred embodiment of the present invention, the esterification reaction will be carried out at pressures less than or equal to 5 mm Hg. A particularly preferred embodiment of the present invention includes conducting the esterification at temperatures of from about 110° C. to about 130° C., under a pressure of from about 1 mm Hg to about 5 mm Hg.

Another option, though not preferred for environmental reasons, which may be employed to assist in the removal of water and other volatiles during the esterification process is the addition of a non-reactive, volatile solvent such as, for example, aliphatic hydrocarbon solvents, aromatics, $C_{3-10}$ alcohols and mixtures thereof.

Removal of esterification by-products, especially water, is preferred during the esterification reaction as this prevents reformation of the tocopherol and/or sterol compound(s) via hydrolysis of the borate esters prior to removal of the low-boiling impurities. Moreover, as the removal proceeds, the reaction proceeds more towards completion, and the potential loss of tocopherol and/or sterol compound(s) due to premature reformation of these compounds through potential condensation reactions is prevented.

In accordance with the present invention, esterification of the tocopherol and/or sterol compound(s) and the alcohol component with one or more boron-containing compounds, wherein the mole ratio of tocopherol, sterol and alcohol to boron is 2.5:1 or higher, prevents unwanted boron solid formation. Thus, additional boron solid removal or recovery and recycling steps, which may be complicated, costly and/or time-consuming, are unnecessary.

After the esterification reaction is completed or taken as close to completion as is desired, the temperature may be raised in order to heat the second mixture to remove remaining low boiling point components, including impurities which co-boil with the unesterified tocopherol and/or sterol compound(s). The temperature is raised to the extent necessary to remove substantially all components boiling at temperatures below the boiling point of the one or more orthoborate esters.

Temperatures during the heating step should be sufficient to remove all, or substantially all, impurities boiling at temperatures lower than the orthoborate esters, i.e., "low boiling point components", including the components of the initial starting composition which have boiling points close to the tocopherol and/or sterol compound(s), i.e., "co-boilers". The precise pressures and temperatures preferably used in accordance with the present invention will vary depending on the distillation points of the impurities present in the composition containing the tocopherol and/or sterol compound(s). Preferred temperatures for the removal of low boiling components, under reduced pressures, are at least about 280° C., more preferably at least about 300° C., and most preferably at least about 305° C. In general, the preferred temperature for removal of low boiling components during the heating step will be from about 60° C. to about 70° C. above the boiling point of the tocopherol at that particular pressure. The boiling point of a starting composition at a particular pressure can be determined through known thermodynamic calculations. The duration of heating of the second mixture may vary, but will be for a time sufficient to allow for distillation of all, or substantially all, low boiling point components. Thus, the heating is generally continued until distillation, or evaporation of the low boiling point components ceases.

However, when the starting composition contains both tocopherol and sterol compounds and isolation of both are desired, the temperature during the heating step is preferably maintained below about 320° C. At temperatures greater than about 320° C., the sterol-containing orthoborate esters formed during the esterification step may decompose, allowing the formation of undesired by-products (e.g. sterol hydrocarbons and/or ring-opened tocopherols), thus reducing the quantity of sterol that may be later recovered.

In accordance with preferred embodiments of the processes according to the present invention, the distillation of the second mixture is carried out under reduced pressures. Preferably, the removal of the low boiling point components will be carried out at pressures less than or equal to 5 mm Hg, and more preferably at pressures less than or equal to 1 mm Hg.

As used herein, the phrase "substantially all" shall mean that degree of removal which is considered sufficient with respect to each component by one skilled in the art, and will generally mean removal of all low boiling point components except for small amounts ranging from undetectable to trace quantities. In general, the purity of the hydroxylic components (i.e., tocopherol and/or sterol compound(s)), obtained by the processes in accordance with the present invention will be 95% or greater, preferably 99% or greater, and most preferably 99.9% or greater.

Co-boilers removed in accordance with the present invention include the non-hydroxyl compounds which boil at or near the boiling points of the tocopherol and/or sterol compound(s), including non-tocopherol, non-sterol components found in the natural sources which may be used as starting compositions in accordance with the present invention, such as, for example, natural esters, hydrocarbons, ketones, pesticides, and fertilizers, particularly steryl hydrocarbons and squalene.

After heating the second mixture at a sufficient temperature for a sufficient amount of time, a residue containing the one or more orthoborate esters will remain. The residue is contacted with any one or more compounds capable of solvolyzing (i.e., cleaving) the orthoborate ester(s) to form the third mixture which contains the tocopherol and/or sterol compound(s), one or more resulting boron-containing compounds (i.e., boron-containing products of solvolysis), and the alcohol originally combined with the starting composition containing the tocopherol and/or sterol compound(s). Examples of suitable compounds capable of solvolyzing the orthoborate ester(s) for use in accordance with the present invention include, but are not limited to, water, methanol, ethanol and mixtures thereof Sources of water, methanol and ethanol may also be used. The one or more resulting boron-containing compounds may include boric acid, and/or trialkyl borate esters depending on which compounds are used for solvolysis. Solvolysis via water (i.e., hydrolysis) will produce boric acid, whereas solvolysis with methanol and/or ethanol will produce the corresponding alkoxy borate esters.

The amount of water, methanol and/or ethanol contacted with the residue containing the orthoborate esters is preferably at least about three moles of water and/or alcohol(s) per mole of boron in order to maximize the amount of tocopherol released via solvolysis and available for recovery. The maximum amount of water and/or alcohol(s) used for solvolysis is limited only for reasons of practicality. In preferred embodiments of the present invention, the amount of water, methanol and/or ethanol may range from about 3.5 to 30 moles per mole of boron to ensure complete solvolysis.

Methanol, ethanol and mixtures thereof are preferred compounds capable of cleaving the orthoborate ester(s) due to the ease of removing the reaction products thus formed, namely methoxy and ethoxy borate esters. Removal of the trimethoxy and triethoxy borate esters may preferably be accomplished via azeotropic distillation. The use of azeotropic distillation allows both methanol and ethanol to be continually added for continued hydrolysis of the orthoborate ester(s), thereby maximizing solvolysis while simultaneously forming and removing the trialkoxy borate esters. Preferably, azeotropic distillation is performed to drive the solvolysis to completion. Thus, in a preferred embodiment of the present invention, azeotropic distillation is performed to drive the solvolysis to completion, with further distillation of the remaining azeotropic solvent mixture and any first mixture-alcohol present in the third mixture, allowing for subsequent isolation of the tocopherol and/or sterol compound(s).

The solvolysis may be conducted at room temperature or higher. When water is used, the temperature should be below reflux to allow for maximum solubility of the boric acid formed. The water and boric acid thus formed can be separated from the tocopherol and/or sterol compound(s) via phase separation. The isolated tocopherol and/or sterol containing phase is then preferably washed with water to ensure complete removal of boric acid. Optionally, the first water wash may be cooled, and solid boric acid recovered and recycled.

Water may be used for hydrolysis at temperatures higher than the boiling point of water by applying pressure to increase the reflux point. By increasing pressure, the temperature may be as high as the equipment will allow.

Any remaining water, ethanol, methanol, and/or original alcohol added to the starting composition, which is not removed via phase separation or through azeotropic distillation when performed, may be removed via further distillation of the solvolyzed third mixture. Such further distillation may be performed at any temperature sufficient to remove both (1) the one or more compounds capable of hydrolyzing the orthoborate ester(s) and (2) the original alcohol added to the starting composition, but below the temperature at which tocopherol compounds and sterol compounds distill.

Thus, after solvolysis and removal of any remaining boron-containing solvolysis products (i.e., boric acid and water, or alkoxy borate esters which did not distill off), the tocopherol and/or sterol compound(s) are recovered. Often, subsequent to solvolysis with accompanying azeotropic distillation, the remaining tocopherol and/or sterol compound(s) are sufficiently pure for further use, and recovery can be performed by simply collecting the tocopherol and/or sterol compound(s).

However, if further purification or enhanced recovery is desired, additional methods including, but not limited to, adsorption chromatography, extraction, ion exchange and fractional distillation of the tocopherol and/or sterol compound(s) may be used.

Where the starting composition contains at least one tocopherol compound and at least one sterol compound and recovery and purification of both is desired, distillation subsequent to recovery can be performed to collect the tocopherol compound(s), thus leaving the sterol compound(s) in the residue.

The present invention will now be illustrated in more detail by reference to the following specific, non-limiting examples.

EXAMPLE 1

A 900.7 g sample containing 55% mixed tocopherols (1.19 mole) and 6% sterols (0.13 mole) was combined with 521.0 g of dodecanol (2.80 mole) and 83.5 g boric acid (1.35 mole). This mixture was heated to 120° C., under 2.9 mm of Hg, with the liberation of water, to form mixed orthoborate esters of the tocopherols, sterols and dodecanol.

The mixed orthoborate esters were then heated to 310° C., under 0.4 to 1.0 mm of Hg, allowing for the distillation of the low boiling point components and co-boilers. The distillate fraction was 30.8% by weight of the mixture and contained $\leq 0.3\%$ of the tocopherols. Almost no tocopherol content was lost to the distillate fraction during removal of the low boiling point components and co-boilers.

The residue fraction contained $\geq 99.7\%$ of the tocopherols and contained <1% of the low boiling point components and co-boilers. The residue fraction contained virtually no ring-opened tocopherols and significantly less co-boilers than products purified by prior art processes.

Three separate samples of the residue were hydrolyzed and washed with water. These samples were combined and the solvent evaporated. The hydrolyzed product was then distilled to separate the dodecanol from the tocopherols and sterols. The product fraction contained 92.7% tocopherols, $\geq 1\%$ co-boilers, with the remainder being sterols.

COMPARATIVE EXAMPLE 1

A 399.9 g sample containing 56% mixed tocopherols (0.54 mole) and 6% sterols (0.06 mole) was combined with 37.0 g of boric acid (0.60 mole). The mixture was heated to 160° C., with the liberation of water. At 160° C., the pressure was reduced to 0.7 mm of Hg to complete the esterification.

The esterified mixture was then heated to 310° C. under vacuum, 0.6–0.9 mm of Hg, to distill the low boiling point components and co-boilers. The distillate fraction contained 2.4% tocopherols and none of the sterols. The tocopherols in the distillate were equivalent to 1.4% of the total tocopherols in the charge. The amount of tocopherol lost to the distillate fraction is significantly higher than in Example 1. Analysis of the residue fraction showed 99.1% of the sterols were destroyed and 5.7% of the tocopherols were ring-opened to form unwanted by-products.

A sample of the residue was dissolved in hexane and mixed with an equal volume of water for 30 minutes to cause hydrolysis. The organic phase was then washed with water four additional times and the solvent evaporated.

The hydrolyzed product was then distilled under vacuum, 0.2–0.4 mm of Hg, to produce 80.5% distillate. The distillate fraction contained 74.2% tocopherols. The purity and yield of the resultant product was significantly lower than Example 1.

COMPARATIVE EXAMPLE 2

A 700.6 g sample containing 56.7% mixed tocopherols (0.96 mole) and 6.9% sterols (0.12 mole) was combined with 22.8 g of boric acid (0.37 mole). The mixture was heated to 160° C., and the pressure reduced to 0.2 mm of Hg, to complete the esterification.

The esterified mixture was then heated to 310° C. under vacuum, 0.4–1.0 mm of Hg, to distill the low boiling point components and co-boilers. The distillate fraction contained 14.8% tocopherols and none of the sterols. The tocopherols in the distillate were equivalent to 9.3% of the total tocopherols in the charge. Again, the amount of tocopherol lost to the distillate fraction is significantly higher than in Example 1.

Analysis of the residue fraction showed 16.3% of the sterols were destroyed and 0.2% of the tocopherols were ring-opened to form unwanted by-products. The residue fraction also contained 6.7% co-boilers.

EXAMPLES 2a–2f

Compositions containing tocopherols and sterols were esterified and stripped of low boiling point components and co-boilers in accordance with Example 1, using various amounts of oleyl alcohol or Guerbitol 16. As shown in Table 1 below, when the overall ratio of alcohol, tocopherol and sterol to boron falls below about 2.5:1, a significantly higher amount of sterols are destroyed and an increasing amount of unwanted ring-opened tocopherols are formed.

TABLE 1

| Ex # | Alcohol | Alcohol (mols) | Toco-pherols (mols) | Sterols (mols) | Boron (mols) | Overall Ratio | Ring-opened tocopherols (%) | Sterols Destroyed (%) |
|---|---|---|---|---|---|---|---|---|
| 2a | None | — | 0.54 | 0.06 | 0.60 | 1.00:1 | 5.7 | 99.1 |
| 2b | None | — | 0.67 | 0.07 | 0.38 | 1.95:1 | 0.8 | 95.1 |
| 2c | Oleyl | 0.45 | 0.42 | 0.03 | 0.44 | 2.05:1 | 0.7 | 80.7 |
| 2d | Oleyl | 0.69 | 0.42 | 0.03 | 0.44 | 2.59:1 | 0.3 | 62.8 |
| 2e | Oleyl | 0.30 | 0.55 | 0.04 | 0.30 | 2.97:1 | 0.3 | 0.8 |
| 2f | Guerbitol 16 | 1.16 | 0.53 | 0.01 | 0.54 | 3.15:1 | 0.1 | 0.0 |

EXAMPLES 3a–3e

Compositions containing tocopherols and sterols were esterified and stripped of low boiling point components and co-boilers in accordance with Example 1, using identical amounts of various alcohols, as listed below in Table 2. The overall ratio of alcohol, tocopherol and sterol to boron in each example was about 3:1. (2:1:1 molar ratio of alcohol:(tocopherol+sterol):boron.)

TABLE 2

| Ex. | Alcohol Used | % of Alcohol Lost to Coboiler Fraction | Viscosity of Borate Ester (cSt @ 60° C.) |
|---|---|---|---|
| 3a | n-butanol | 100.0 | — |
| 3b | n-octanol | 98.3 | 6717.6 |
| 3c | n-decanol | 77.5 | 1382.4 |
| 3e | n-dodecanol | 26.2 | 103.5 |
| 3f | Guerbitol 16 | 7.6 | 78.2 |

As can be seen from the data in Table 2, when using alcohols more volatile than n-dodecanol, a high loss of alcohol and high product viscosity result.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process for purifying compounds, said process comprising:
   (a) providing a first mixture comprising at least one compound selected from the group consisting of tocopherol compounds and sterol compounds, and an alcohol having from about 10 to about 30 carbon atoms;
   (b) reacting the first mixture with one or more boron-containing compounds selected from the group consisting of boric acid, alkoxy borates, alkoxy boroxines, phenoxy borates and phenoxy boroxines to form a second mixture comprising one or more orthoborate esters, wherein the mole ratio of combined tocopherol, sterol and alcohol to boron is at least about 2.5:1;
   (c) heating the second mixture to remove low boiling point components to form a residue comprising the one or more orthoborate esters;
   (d) contacting the residue with one or more compounds capable of solvolyzing the one or more orthoborate esters to form a third mixture comprising one or more resulting boron-containing compounds, the alcohol and the at least one compound selected from the group consisting of tocopherol compounds and sterol compounds; and (e) recovering the at least one compound selected from the group consisting of tocopherol compounds and sterol compounds.

2. The process according to claim 1, wherein the one or more compounds capable of solvolyzing the one or more orthoborate esters comprises water.

3. The process according to claim 2, wherein recovering the at least one compound selected from the group consisting of tocopherol compounds and sterol compounds comprises phase separation.

4. The process according to claim 1, wherein the one or more compounds capable of solvolyzing the one or more orthoborate esters comprises a cleaving component selected from the group consisting of methanol, ethanol, and mixtures thereof.

5. The process according to claim 4, wherein recovering the at least one compound selected from the group consisting of tocopherol compounds and sterol compounds comprises azeotropic distillation.

6. The process according to claim 1, wherein said composition comprises at least one tocopherol compound and at least one sterol compound, said process further comprising separating the at least one tocopherol compound and the at least one sterol compound subsequent to step (e).

7. The process according to claim 1, wherein said alcohol has from about 12 to about 26 carbon atoms.

8. The process according to claim 1, wherein said alcohol has from about 12 to about 20 carbon atoms.

9. The process according to claim 1, wherein said alcohol is selected from the group consisting of dodecanol, tetradecanol, hexadecanol, octadecanol, oleyl alcohol, isostearyl alcohol, 2-hexyldecanol and mixtures thereof.

10. The process according to claim 1, wherein the ratio of combined tocopherol, sterol and alcohol to boron is at least about 3:1.

11. The process according to claim 7, wherein the ratio of combined tocopherol, sterol and alcohol to boron is at least about 3:1.

12. The process according to claim 8, wherein the ratio of combined tocopherol, sterol and alcohol to boron is at least about 3:1.

13. The process according to claim 9, wherein the ratio of combined tocopherol, sterol and alcohol to boron is at least about 3:1.

14. The process according to claim 1, wherein at least a portion of the heating step (c) is carried out at a pressure below standard atmospheric pressure.

15. The process according to claim 1, wherein at least portions of the reaction step (b) and the heating step (c) are carried out at pressures below standard atmospheric pressure.

16. The process according to claim 14, wherein step (c) is carried out at a pressure less than or equal to 5 mm Hg.

17. The process according to claim 15, wherein steps (b) and (c) are carried out at a pressure less than or equal to 5 mm Hg.

18. The process according to claim 1, wherein step (c) is camred out at or above a temperature which is about 60° C. greater than the boiling point of the at least one compound selected from the group consisting of tocopherol compounds and sterol compounds.

19. The process according to claim 1, wherein heating the second mixture comprises a preheating step to remove residual water formed during formation of the one or more orthoborate esters, and further heating at a temperature higher than the preheating temperature to remove remaining low boiling point components.

20. The process according to claim 1, further comprising subjecting the at least one compound selected from the group consisting of tocopherol compounds and sterol compounds to an activated carbon pretreatment prior to step (a).

21. The process according to claim 1, further comprising subjecting the first mixture to an activated carbon pretreatment prior to step (b).

22. The process according to claim 20, wherein the activated carbon pretreatment comprises stirring the composition with an activated carbon powder for at least 1 minute at a temperature of at least about 50° C.

23. The process according to claim 22, wherein the activated carbon powder is present in an amount of at least 0.25 weight percent based on the total weight of the composition.

24. The process according to claim 21, wherein the activated carbon pretreatment comprises stirring the first mixture with an activated carbon powder for at least 1 minute at a temperature of at least about 50° C.

25. The process according to claim 24, wherein the activated carbon powder is present in an amount of at least 0.25 weight percent based on the total weight of the composition.

26. The process according to claim 1, further comprising subjecting the at least one compound selected from the group consisting of tocopherol compounds and sterol compounds to an activated carbon treatment subsequent to step (e).

27. The process according to claim 26, wherein the activated carbon treatment comprises stirring the at least one compound with an activated carbon powder for at least 1 minute at a temperature of at least about 50° C.

28. The process according to claim 27, wherein the activated carbon powder is present in an amount of at least 0.25 weight percent based on the total weight of the at least one compound.

29. A process for purifying compounds, said process comprising:

(a) providing a first mixture comprising at least one compound selected from the group consisting of tocopherol compounds and sterol compounds, and oleyl alcohol;

(b) reacting the first mixture with boric acid to form a second mixture comprising one or more orthoborate esters, wherein the mole ratio of combined tocopherol, sterol and oleyl alcohol to boron is at least about 3:1;

(c) heating the second mixture to a temperature which is at least about 60° C. greater than the boiling point of the at least one compound selected from the group consisting of tocopherol compounds and sterol compounds, under reduced pressure, whereby a residue comprising the one or more orthoborate esters is formed;

(d) contacting the residue with one or more compounds capable of solvolyzing the one or more orthoborate esters to form a third mixture comprising one or more resulting boron-containing compounds, the oleyl alcohol and the at least one compound selected from the group consisting of tocopherol compounds and sterol compounds; and (e) separating the one or more resulting boron-containing compounds from the third mixture.

30. The process according to claim 29, wherein said first mixture comprises at least one tocopherol compound and at least one sterol compound, said process further comprising separating the at least one tocopherol compound and the at least one sterol compound subsequent to step (d).

31. A process for purifying compounds, said process comprising:
   (a) combining a composition comprising at least one compound selected from the group consisting of tocopherol compounds and sterol compounds with one or more boron-containing compounds selected from the group consisting of boric acid, alkoxy borates, alkoxy boroxines, phenoxy borates and phenoxy boroxines to form a mixture comprising one or more borate esters;
   (b) heating the mixture to remove low boiling point components to form a residue comprising the one or more borate esters;
   (c) contacting the residue with one or more compounds capable of hydrolyzing the one or more borate esters to form a second mixture comprising one or more resulting boron-containing compounds and the at least one compound selected from the group consisting of tocopherol compounds and sterol compounds;
   (d) separating the one or more resulting boron-containing compounds and the at least one compound selected from the group consisting of tocopherol compounds and sterol compounds; and
   (e) subjecting the at least one compound selected from the group consisting of tocopherol compounds and sterol compounds to an activated carbon treatment.

32. The process according to claim 31, wherein said composition comprises at least one tocopherol compound and at least one sterol compound, said process further comprising separating the at least one tocopherol compound and the at least one sterol compound subsequent to step (d).

33. The process according to claim 32, wherein at least a portion of the heating step (c) is carried out at pressures below standard atmospheric pressure.

34. The process according to claim 32, wherein at least portions of the reaction step (b) and the heating step (c) are carried out at pressures below standard atmospheric pressure.

35. The process according to claim 33, wherein step (c) is carried out at a pressure less than or equal to 5 mm Hg.

36. The process according to claim 34, wherein steps (b) and (c) are carried out at a pressure less than or equal to 5 mm Hg.

37. The process according to claim 32, wherein step (c) is carried out at a temperature which is about 60° C. greater than the boiling point of the at least one compound selected from the group consisting of tocopherol compounds and sterol compounds.

38. A composition comprising a mixture of monoalkyl-ditocopherol orthoborate esters, dialkyl-monotocopherol orthoborate esters, and trialkyl borate esters.

39. The composition according to claim 38, further comprising monoalkyl-disterol orthoborate esters and dialkyl-monosterol orthoborate esters.

40. The composition according to claim 38, wherein said alkyl moieties have from about 10 to about 30 carbon atoms.

41. The composition according to claim 38, wherein said alkyl rail moieties have from about 12 to about 26 carbon atoms.

42. The composition according to claim 38, wherein said alkyl moieties have from about 16 to about 20 carbon atoms.

43. The composition according to claim 38, wherein said alkyl moieties have 18 carbon atoms.

44. The composition according to claim 43, wherein said alkyl moieties have an unsaturated carbon-carbon double bond.

45. A composition prepared by a process comprising:
   (a) providing a first mixture comprising at least one compound selected from the group consisting of tocopherol compounds and sterol compounds, and an alcohol having from about 10 to about 30 carbon atoms;
   (b) reacting the first mixture with one or more boron-containing compounds selected from the group consisting of boric acid, alkoxy borates, alkoxy boroxines, phenoxy borates and phenoxy boroxines to form a second mixture comprising one or more orthoborate esters, wherein the mole ratio of combined tocopherol, sterol and alcohol to boron is at least about 2.5:1; and
   (c) heating the second mixture to remove low boiling point components to form a mixture comprising the one or more orthoborate esters.

46. The composition according to claim 45, wherein said alcohol has from about 12 to about 26 carbon atoms.

47. The composition according to claim 45, wherein said alkyl moieties have from about 16 to about 20 carbon atoms.

48. The composition according to claim 45, wherein said alcohol is selected from the group consisting of hexadecanol, octadecanol, oleyl alcohol and mixtures thereof.

49. The composition according to claim 45, wherein the ratio of combined tocopherol, sterol and alcohol to boron is at least about 3:1.

50. The composition according to claim 46, wherein the ratio of combined tocopherol, sterol and alcohol to boron is at least about 3:1.

51. The composition according to claim 47, wherein the ratio of combined tocopherol, sterol and alcohol to boron is at least about 3:1.

52. The composition according to claim 48, wherein the ratio of combined tocopherol, sterol and alcohol to boron is at least about 3:1.

* * * * *